(12) United States Patent
Pike

(10) Patent No.: US 6,411,378 B1
(45) Date of Patent: Jun. 25, 2002

(54) MASK, STRUCTURES, AND METHOD FOR CALIBRATION OF PATTERNED DEFECT INSPECTIONS

(75) Inventor: Christopher Lee Pike, Fremont, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/484,655

(22) Filed: Jan. 24, 2000

(51) Int. Cl.[7] .............................................. G01N 21/00
(52) U.S. Cl. ............................... 356/237.5; 356/237.2; 356/237.4; 356/237.5; 356/394
(58) Field of Search .......................... 356/237.2, 237.3, 356/237.4, 237.5, 243.1, 243.4, 394; 250/252.1, 562, 563, 572, 559.48, 559.42, 599.48

(56) References Cited

U.S. PATENT DOCUMENTS

| | | | | |
|---|---|---|---|---|
| 4,386,850 A | * | 6/1983 | Leahy | 356/237.4 |
| 5,383,018 A | * | 1/1995 | Sadjadi | 356/237.5 |
| 5,471,066 A | * | 11/1995 | Hagiwara | 356/237.5 |
| 5,691,812 A | * | 11/1997 | Bates et al. | 356/243.4 |
| 6,246,472 B1 | * | 6/2001 | Yoda et al. | 356/237.2 |

* cited by examiner

Primary Examiner—Frank G. Font
Assistant Examiner—Sang H. Nguyen
(74) Attorney, Agent, or Firm—Davis Chin

(57) ABSTRACT

There is provided an on-wafer apparatus and method for calibrating the sensitivity of a patterned wafer defect inspection tool during set-up which is used to detect defects on the surface of a semiconductor wafer during the stages of a fabrication process. A semiconductor wafer which is to be inspected for defects is provided. A calibration structure having known defects is introduced on a selected area of the semiconductor wafer which is to be inspected prior to, the inspection. The calibration structure includes a plurality of intentionally-introduced defects each being of a progressively smaller size dimension. Calibration of the sensitivity of the defect inspection tool is accomplished by scanning the semiconductor wafer with the calibration structure in order to determine the defects which are known to exist. As a result, there is provided a universal calibration method which allows an operator to know the smallest size defect which is detected by the defect inspection tool for each inspection in the fabrication process.

10 Claims, 3 Drawing Sheets

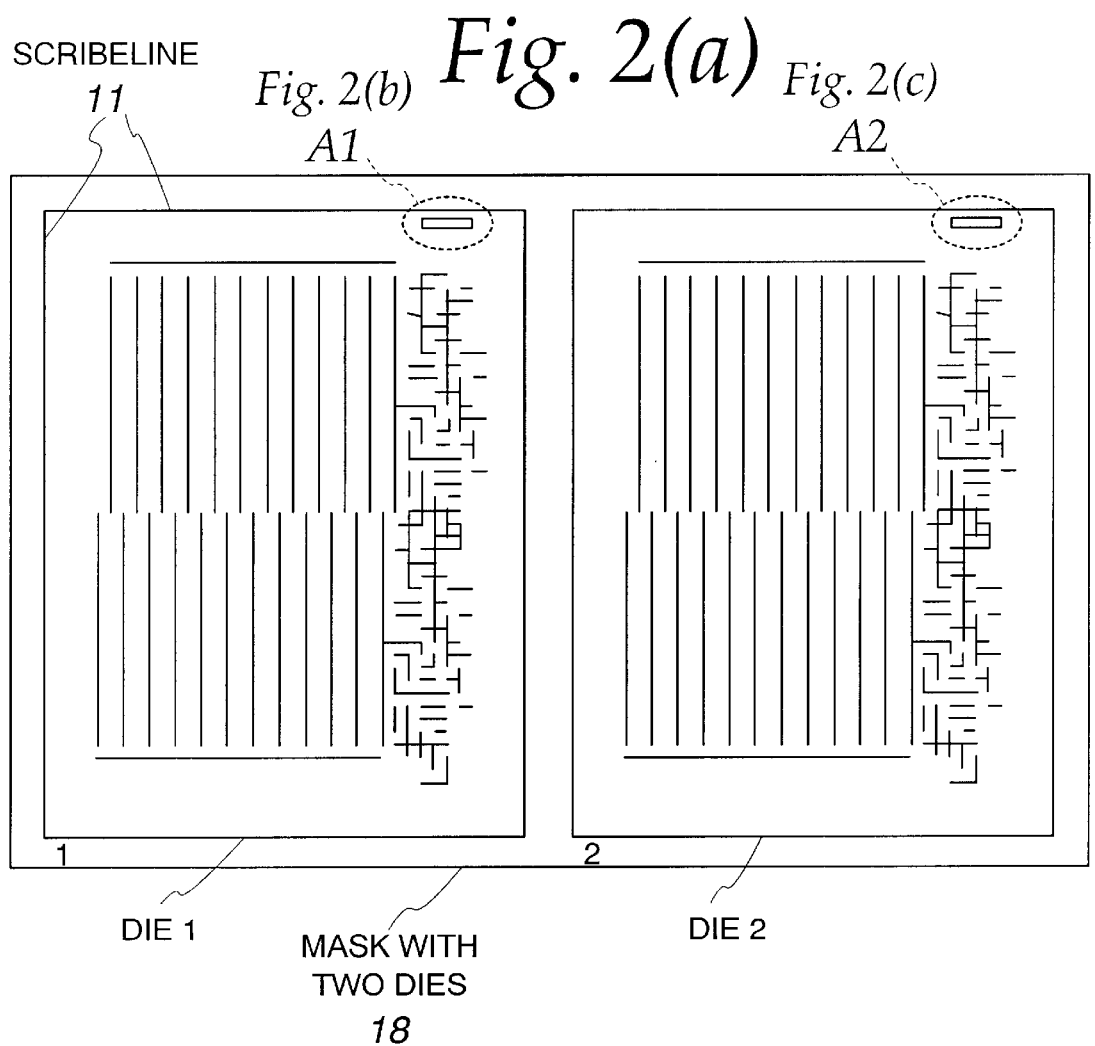
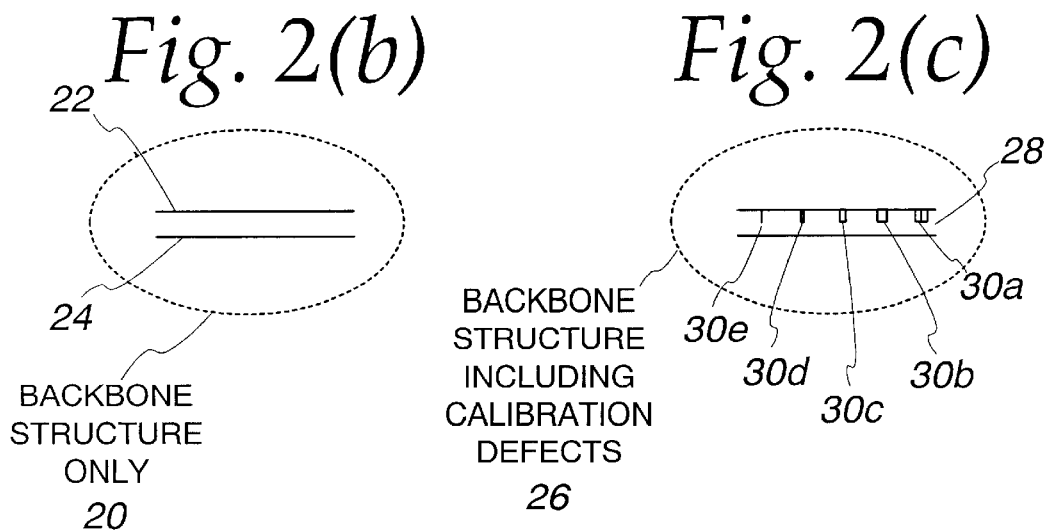

MASK, STRUCTURES, AND METHOD FOR CALIBRATION OF PATTERNED DEFECT INSPECTIONS

BACKGROUND OF THE INVENTION

This invention relates generally to wafer defect detection systems and more particularly, it relates to an apparatus and method for introducing an on-wafer calibration structure on a semiconductor wafer to be inspected for use with a patterned wafer defect detection system so as to quickly and accurately calibrate the sensitivity of the detection system. Specifically, the present invention has particular application in patterned wafer defect detection systems or defect inspection tools which use image subtraction to detect defects on the surface of the semiconductor wafer.

As is generally known, the fabrication process of semiconductor integrated circuits involves a sequence of stages or steps which are used to convert a wafer of semiconductor material into a device(s) having a plurality of layers in which each layer has a particular pattern of circuit elements and interconnections. Since defects on the surface of a wafer layer that has been patterned will be detrimental to the quality of the manufactured semiconductor devices, semiconductor device manufacturers have utilized extensively defect detection systems for detecting defects on processed wafers of semiconductor material during each stage of the fabrication process. Thus, patterned defect inspections are regularly performed a number of times during the manufacturing process of a semiconductor device.

The defect detection systems or defect inspection tools are typically capable of being operated in two modes of operation so as to inspect the wafer for defects: (1) array mode and (2) random mode. In the array mode, a highly repetitive set of structures (such as those typically found in a RAM or memory device) are inspected by defining a cell comprising a subset of the repeating structure. This cell is compared to the cells on both the left and right sides of it and defects are detected as a difference between the subtraction of one cell from its neighboring cell. In the random mode, random structures (such as those found in a logic device) are inspected by defining an entire die or portion thereof) as a cell. This die is compared to the dice on both the left and right sides of it and defects are detected as a difference between the subtraction of one die from its neighboring die.

In order to accurately measure and detect the defects on the semiconductor wafer, the defect inspection tool must be accurately calibrated so as to prevent false detections. Therefore, once the cells are defined for the inspection, the sensitivity of the defect inspection tool must be adjusted or tuned in order to maximize the detection of the processing defects. Further, this adjustment must be performed repeatedly and individually on each defect inspection so as to optimize its sensitivity for detecting of the processing defects at each stage of the fabrication process at that point. Since the sensitivity of the defect inspection tool is a function of a number of factors, such as type of defects on the semiconductor wafer, number of patterned layers formed on the wafer, and so on, this complicates the calibration process for different wafers and for different types of wafer inspection tools.

The current procedure involves an iterative process of increasing the sensitivity of the defect inspection tool, scanning the wafer to detect for false defects, decreasing slightly the sensitivity, and scanning the wafer again to check that the false defects are no longer detected. As can be seen, this prior art technique is a very time-consuming operation during the different stages of the fabrication process and thus increases manufacturing costs.

The inventor is unaware of a calibration method which allows an operator or user of a defect inspection tool to know the smallest size defect that is detected by the defect inspection tool for each inspection in a semiconductor manufacturing process. Accordingly, it would be desirable to provide an on-wafer method and apparatus for calibrating the sensitivity of a patterned defect inspection tool during set-up so as to detect defects of known sizes. Further, it would be expedient that the on-wafer method and apparatus for calibrating the sensitivity of the patterned defect inspection tool allow direct comparison of different inspection tools at the various stages of the fabrication process. This is accomplished in the present invention by introducing a calibration structure having intentionally-introduced defects onto the wafer which is scanned during the defect inspection recipe setup or during each defect inspection.

SUMMARY OF THE INVENTION

Accordingly, it is a general object of the present invention to provide an apparatus and method for introducing an on-wafer calibration structure on a semiconductor wafer to be inspected which overcomes the disadvantages of the prior art calibration techniques.

It is an object of the present invention to provide an improved apparatus and method for introducing an on-wafer calibration structure on a semiconductor wafer to be inspected.

It is another object of the present invention to provide an apparatus and method for introducing an on-wafer calibration structure on a semiconductor wafer to be inspected for use with a wafer defect detection tool so as to quickly and accurately calibrate the sensitivity thereof.

It is still another object of the present invention to provide an apparatus and method for introducing an on-wafer calibration structure on a semiconductor wafer to be inspected which includes a plurality of intentionally-introduced defects each being of a progressively smaller size dimension.

In a preferred embodiment of the present invention, there is provided an on-wafer method for calibrating the sensitivity of a patterned wafer defect inspection tool during setup which is used to detect defects on the surface of a semiconductor wafer during the stages of a fabrication process. A semiconductor wafer which is to be inspected for defects is provided. A calibration structure is introduced which has known defects disposed on a selected area of the semiconductor wafer which is to be inspected for defects prior to the inspection. The semiconductor wafer with the calibration structure is loaded into the defect inspection tool.

The semiconductor wafer is aligned with respect to the defect inspection tool. Areas of the semiconductor wafer to be inspected are determined. The sensitivity of the defect inspection tool is adjusted to the desired scanning sensitivity setting. The sensitivity of the defect inspection tool is calibrated by scanning the semiconductor wafer with the calibration structure in order to determine the known defects which can be detected.

BRIEF DESCRIPTION OF THE DRAWINGS

These and other objects and advantages of the present invention will become more fully apparent from the following detailed description when read in conjunction with the accompanying drawings with like reference numerals indicating corresponding parts throughout, wherein:

FIG. 2(a) is an enlarged view of the encircled area A of FIG. 1, containing a mask having two adjacent dice areas formed of a die area 1 and a die area 2;

FIG. 2(b) is an enlarged view of the encircled area A1 of FIG. 2(a), illustrating a backbone structure;

FIG. 2(c) is an enlarged view of the encircled area A2 of FIG. 2(a), illustrating a backbone structure and a random mode calibration structure;

DESCRIPTION OF THE PREFERRED EMBODIMENTS

One of the problems in using a wafer defect detection system or defect inspection tool (scanners) for detecting defects on processed wafers of semiconductor material during the different stages or steps of the fabrication process is the very time-consuming task of accurately calibrating of the sensitivity of the defect inspection tool so as to prevent false detections. The purpose of the instant invention is to provide a universal on-wafer apparatus and method of calibrating the sensitivity of a defect detection system during set-up to detect defects of known sizes. This improves the signal-to-noise ratio of the defect inspection and permits an operator or user to know what size of defect the defect inspection tool is capable of detecting. As a result, there is provided a more accurate modeling of product yield since the minimum detectable defect size is known for each defect inspection. Information on the defect size is important due to the fact that the likelihood of a defect "killing" a die (e.g., so as to render it non-functional) is typically a function of the defect size.

In view of this, the inventor of the present invention has developed an on-wafer calibration structure which is introduced onto the semiconductor wafer that is scanned during the defect inspection recipe setup or during each defect inspection. The calibration structure is comprised of a small intentionally-introduced defect (or a series of defects of different sizes) which allows an operator or user to tune the sensitivity of the defect inspection tool to detect the small defects.

Figure 1:
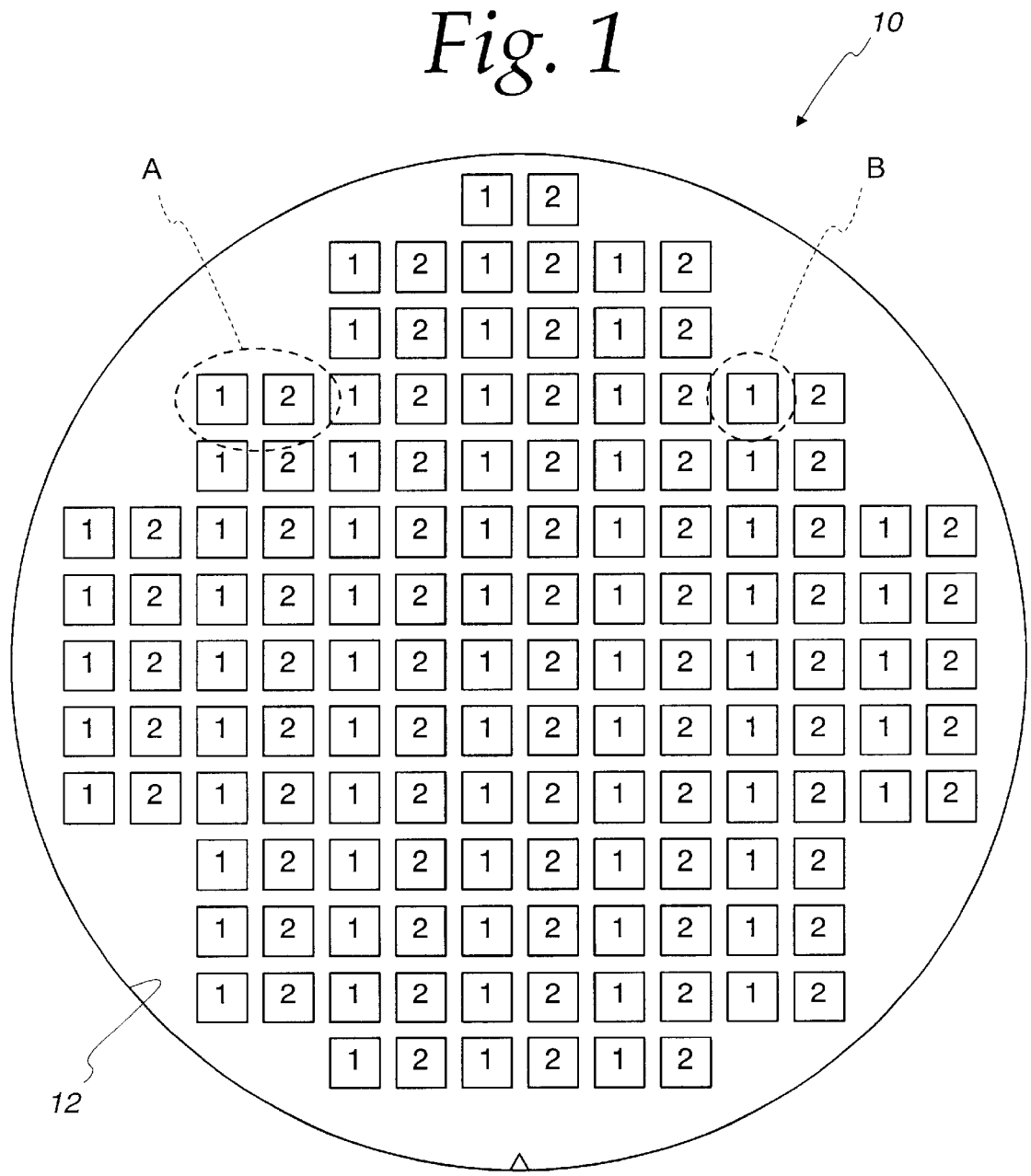
FIG. 1 is a top plan view of a semiconductor wafer having a plurality of divided or sectored sections or dice areas in which a calibration structure of the present invention is employed.

Referring now to FIG. 1 of the drawings, there is illustrated a top plan view of a semiconductor wafer 10 which is divided or sectored into a plurality of dice areas or regions labeled 1 and 2. The vertical and horizontal lines used to form the regions 1, 2 are actually the scribelines 11 (FIG. 2(a) and FIG. 3(a)) marked on the wafer 10. The dice areas 1, 2 do not extend all the way to the periphery of the wafer so that a small space is left around the outer edge 12 of the wafer.

FIG. 2(a) is an enlarged view of the encircled area A of FIG. 1 which illustrates a mask 18 having two adjacent dice areas formed by die 1 and die 2. FIG. 2(b) is an enlarged view of the encircled area A1 of FIG. 2(a) which illustrates a backbone structure 20 formed by two parallel, spaced-apart lines 22 and 24 in the die 1. FIG. 2(c) is an enlarged view of the encircled area A2 of FIG. 2(a) which illustrates a backbone structure 26 and a calibration structure 28 for use with a defect inspection tool (not shown) being operated in the random mode.

As will be recalled, in the random mode of operation (FIG. 1), each entire die (i.e., die 1) is compared to both the adjacent left and right dice (i.e., die 2) in the horizontal direction only. The defect inspection tool subtracts a "candidate" image from a reference image and any difference will be labeled as a defect. As a consequence, the backbone structure 20 (26) is placed in both dice (die 1 and die 2) in FIG. 2(a), but the calibration structure 28 is placed only in one of the two adjacent dice (i.e., die 2). Thus, the random mode of operation can only be used on a mask containing two or ore dice.

In particular, the calibration structure 28 is only present in every other die on the wafer 10 and therefore will be detected as defects during the defect inspection. The calibration structure may be comprised of either a single intentionally-introduced defect or a series of defects with different sizes which allows an operator or user to tune the sensitivity of the defect inspection tool in order to detect the small defect(s). The calibration structure is located on a selected area on the semiconductor wafer and may be added to any mask used in the course of a normal photolithography process. Alternatively, the calibration structure may be added to any other mask used during the fabrication process, such as a reflective mask or through direct writing into the resist using ion/electron beam projection.

In the preferred embodiment of FIG. 2(c), the calibration structure 28 is formed of a plurality (five) of intentionally-introduced defects 30a–30e each being of a progressively smaller size dimension which are arranged in a serial alignment. The adjacent ones of the defects 30a–30e are disposed in an equally spaced-apart relationship. In other words, the defect 30b is made to be smaller in size than the defect 30a, the defect 30c is made to be smaller in size than the defect 30b, and so on. In this manner, the sensitivity of the defect inspection tool for each individual inspection can be adjusted so as to detect the desired size defect of the calibration structure at the time the inspection is being performed.

Once the adjustment of the sensitivity setting for a particular defect inspection tool is completed, it will then be known the size of the defect that can be detected during the subsequent inspection of other different wafers since the same calibration structure is introduced on each wafer to be inspected. Thus, the calibration structure for a different defect inspection tool of the same type involves only adjusting the known sensitivity settings for corresponding defect sizes. Further, a direct comparison of the performance of different defect inspection tools can be made when applied during a particular stage of the fabrication process since the defect detection capability is determined by a universal calibration structure formed on the wafer which is scanned during the defect inspection recipe setup or during each defect inspection.

Figure 3A:
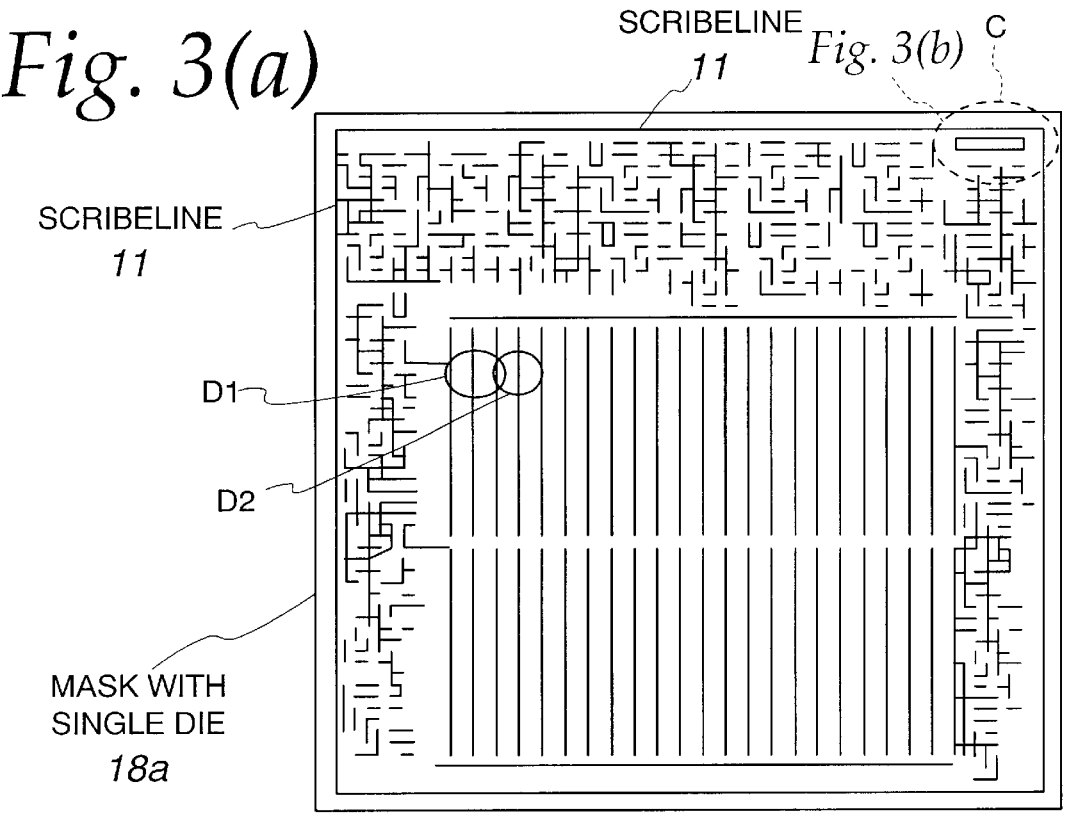
FIG. 3(a) is an enlarged view of the encircled area B of FIG. 1, illustrating a mask having single die area 1.
Figure 3B:
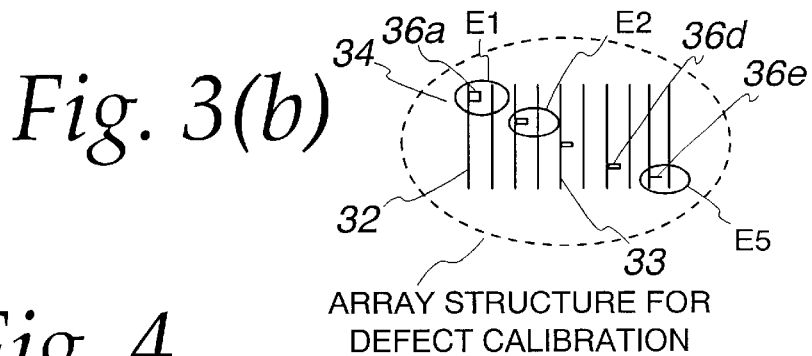
FIG. 3(b) is an enlarged view of the encircled area C of FIG. 3(a), illustrating a backbone structure and an array mode calibration structure.

FIG. 3(a) is an enlarged view of the encircled area B of FIG. 1 which illustrates a mask 18a having a single die area formed by die 1. FIG. 3(b) is an enlarged view of the encircled area C of FIG. 3(a) which depicts a backbone structure 32 and a calibration structure 34 for use with a defect inspection tool being operated in the array mode. As previously pointed out, in the array mode of operation adjacent cells defining the subset of the repeating pattern are compared instead of the entire die to detect the defect. Thus, the array mode calibration structure 34 is placed on each and every die of the mask. Accordingly, the array mode of operation can be used on the mask containing only one die. As shown in FIG. 3(a), each cell (i.e., D1) of the single die 1 is compared to both the adjacent left and right cells (i.e., D2) in the horizontal direction.

As can be seen from FIG. 3(b), the backbone structure 32 is formed by a plurality of equally-spaced vertical parallel lines 33. The calibration structure 34 is formed of a plurality of defects 36a–36e, each being of a progressively smaller size dimension which are arranged in a diagonal manner between the respective vertical parallel lines of the backbone structure 32. The defect 36b is made to be smaller in size than the defect 36a, the defect 36c is made to be smaller in size than the defect 36b, and so on. The defects 36a–36e are arranged such that there is no more than one defect per cell with the cell size being larger than the minimum size definable by the defect inspection tool. In other words, the defects 36a–36e are located in separate corresponding cells E1–E5. Alternatively, more than one defect may be placed in a single cell if the defects are spaced sufficiently far apart from each other so as to permit them to be detected separately.

Figure 4:
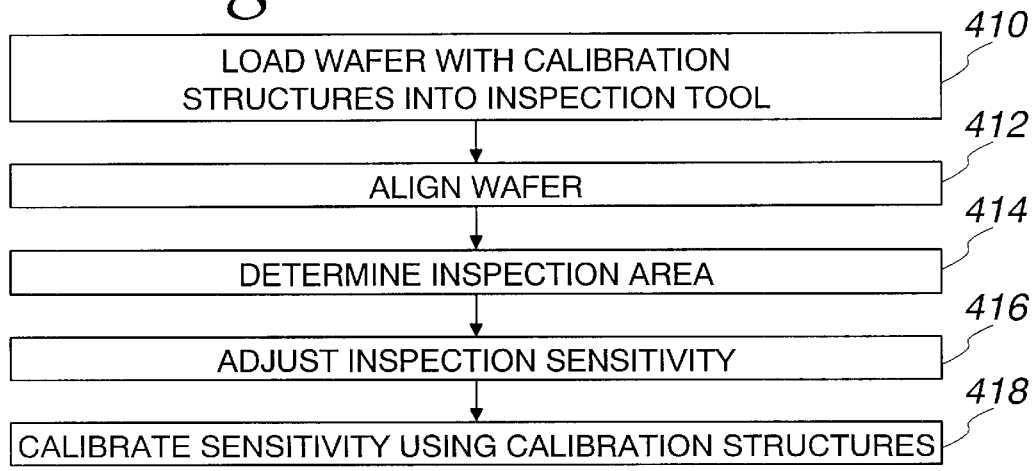
FIG. 4 is a flow chart, showing the steps for calibrating a defect inspection tool utilizing the calibration structure of FIG. 2(c) or FIG. 3(b), according to the method of the present invention.

In another aspect of the present invention, there is provided a method for calibrating the sensitivity of the patterned defect inspection tool by using the on-wafer calibration structure illustrated in FIG. 2(c) or FIG. 3(b). In FIG. 4, there is shown a flow chart which depicts the steps for calibrating the sensitivity of a defect inspection tool in accordance with the method of the present invention.

In block 410, the present method is started by loading a semiconductor wafer with either the random mode calibration structure 28 of FIG. 2(c) or the array mode calibration structure 34 of FIG. 3(b) into a wafer defect detection system or defect inspection tool. If the dice on the wafer contains random logic circuitry, the defect inspection tool will be operated in the random mode so as to detect defects on the wafer with the calibration structure 28. On the other hand, if the dice on the wafer contain circuitry with repeating patterns, then the defect inspection tool will be operated in the array mode so as to detect defects on the wafer with the calibration structure 34.

Next, in block 412 the wafer is aligned in the defect inspection tool so as to allow it to accurately and repeatably determine defect positions. Then, in the block 414 the appropriate inspection areas of the die or dice will be determined so that they will be scanned and compared during the defect inspection. In the block 416, the sensitivity of the defect inspection tool is adjusted by the operator to the desired scanning sensitivity.

Finally, in block 418 the calibration of the sensitivity of the defect inspection tool is performed. This is accomplished by scanning the wafer containing the different sizes of defects which are known to exist on the calibration structure. Once the defect inspection of the wafer is completed, it will be known the "smallest size defect" which can be detected by the defect inspection tool. If this is the defect size desired to be detected for subsequent inspections, the sensitivity settings on the defect inspection tools are left at the current settings and the defect inspection tool is calibrated.

If some other defect size is desired to be the "smallest size defect," then the sensitivity settings are adjusted so as to tune the defect inspection tool in the block 418 and the wafer is scanned again. This is repeated until the scan detects the desired defect size from one of the different sizes of defects which are known to exist in the calibration structure.

From the foregoing detailed description, it can thus be seen that the present invention provides an on-wafer method for calibrating the sensitivity of a patterned wafer defect inspection tool during set-up which is used to detect defects on the surface of a semiconductor wafer during the stages of a fabrication process. A calibration structure having known defects are disposed on a selected area on the semiconductor wafer which is to be inspected for defects prior to the inspection. The calibration structure includes a plurality of intentionally-introduced defects each being a progressively smaller size dimension.

While there has been illustrated and described what are at present considered to be preferred embodiments of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiments disclosed as the best modes contemplated for carrying out the invention, but that the invention will include all embodiments falling within the scope of the appended claims.

What is claimed is:

1. An on-wafer method for calibrating the sensitivity of a patterned wafer defect inspection tool during set-up which is used to detect defects on the surface of a semiconductor wafer during the stages of a fabrication process, said method comprising the steps of:

providing a semiconductor wafer which is to be inspected for defects;

introducing a calibration structure having a plurality of intentionally-introduced defects each being of a progressively smaller size dimension on a selected area of the semiconductor wafer which is to be inspected for defects prior to the inspection;

loading the semiconductor wafer with the calibration structure in to the defect inspection tool;

aligning the semiconductor wafer with respect to the defect inspection tool;

determining areas o f the semiconductor wafer to be inspected;

adjusting the sensitivity of the defect inspection tool to a desired scanning sensitivity setting; and calibrating the sensitivity of the defect inspection tool by scanning the semiconductor wafer with the calibration structure in order to determine the defect size from one of the plurality of intentionally-introduced defects that can be detected by the defection inspection tool.

2. An on-wafer method as claimed in claim 1, wherein said plurality of intentionally-introduced defects s are arranged in a serial alignment when the defect inspection tool is operated in a random mode of operation.

3. An on-wafer method as claimed in claim 2, wherein adjacent ones of said plurality of defects are disposed at an equally spaced-apart relationship.

4. An on-wafer method as claimed in claim 1, wherein said plurality of intentionally-introduced defects are arranged in a diagonal manner when the defect inspection tool is operated in an array mode of operation.

5. An on-wafer method as claimed in claim 4, wherein adjacent ones of said plurality of defects are disposed sufficiently apart from each other so as to permit them to be detected separately.

6. An on-wafer apparatus for use in calibrating the sensitivity of a patterned wafer defect inspection tool during set-up which is used to detect defects on the surface of a semiconductor wafer during the stages of a fabrication process, said apparatus comprising:

a semiconductor wafer which is to be inspected for defects;

a calibration structure having a plurality of intentionally-introduced defects each being of a progressively smaller size dimension formed on a selected area of the said semiconductor wafer which is to be inspected for defects prior to the inspection;

said semiconductor wafer with the calibration structure being loaded into the defect inspection tool;

said semiconductor wafer being aligned with respect to said defect inspection tool;

areas of said semiconductor wafer to be inspected being determined;

said defect inspection tool having a sensitivity adjustment which is adjusted to a desired scanning sensitivity setting; and the sensitivity of said defect inspection tool being calibrated by scanning the semiconductor wafer with the calibration structure in order to determine the defect size from one of the plurality of intentionally-introduced defects that can be detected by the defection inspection tool.

7. An on-wafer apparatus as claimed in claim 6, wherein said plurality of intentionally-introduced defects are arranged in a serial alignment when the defect inspection tool is operated in a random mode of operation.

8. An on-wafer apparatus as claimed in claim 7, wherein adjacent ones of said plurality of defects are disposed at an equally spaced-apart relationship.

9. An on-wafer apparatus as claimed in claim 6, wherein said plurality of intentionally-introduced defects are arranged in a diagonal manner when the defect inspection tool is operated in an array mode of operation.

10. An on-wafer apparatus as claimed in claim 9, wherein adjacent ones of said plurality of defects are disposed sufficiently apart from each other so as to permit them to be detected separately.

* * * * *

UNITED STATES PATENT AND TRADEMARK OFFICE
CERTIFICATE OF CORRECTION

PATENT NO. : 6,411,378 B1 Page 1 of 1
DATED : June 25, 2002
INVENTOR(S) : Christopher L. Pike It is certified that error appears in the above-identified patent and that said Letters Patent is hereby corrected as shown below:

<u>Title page,</u>
Item [57], ABSTRACT
Line 8, delete -- , --.

<u>Column 4,</u>
Line 17, change "ore" to -- more --.

<u>Column 6,</u>
Line 42, change "in to" to -- into --.
Line 45, change "o f" to -- of --.
Line 55, delete "s".

Signed and Sealed this

Fifteenth Day of October, 2002

Attest:

Attesting Officer

JAMES E. ROGAN
*Director of the United States Patent and Trademark Office*